United States Patent [19]

Dorton

[11] 4,234,086
[45] Nov. 18, 1980

[54] APPARATUS FOR HANDLING SOILED SURGICAL SPONGES

[76] Inventor: Howard E. Dorton, 108 E. Maxwell St., Lexington, Ky. 40508

[21] Appl. No.: 81,172

[22] Filed: Oct. 2, 1979

Related U.S. Application Data

[63] Continuation-in-part of Ser. No. 31,839, Apr. 20, 1979, abandoned.

[51] Int. Cl.³ .................... B65D 30/22; B65D 33/02; B65D 33/14; B65D 85/00
[52] U.S. Cl. ........................................ 206/362; 150/1; 206/286; 206/554; 206/632; 206/806; 229/56
[58] Field of Search ............ 128/1 R, DIG. 5; 150/1, 150/34, 52 R; 190/13 F, 41 B; 206/286, 288, 299, 361–362, 370, 390, 440, 484, 526, 554, 806, 820, 632; 229/53, 56, 62, 69

[56] References Cited

U.S. PATENT DOCUMENTS

| | | | |
|---|---|---|---|
| 3,587,845 | 6/1971 | Wing | 206/554 |
| 3,727,829 | 4/1973 | Huni | 229/62 |
| 3,749,237 | 7/1973 | Dorton | 150/1 |
| 3,858,789 | 1/1975 | Verbeke | 229/62 |
| 3,884,412 | 5/1975 | Price | 229/69 |
| 3,979,050 | 9/1976 | Cilia | 206/390 |

*Primary Examiner*—William T. Dixson, Jr.
*Attorney, Agent, or Firm*—Robert A. Ostmann

[57] ABSTRACT

The disclosure concerns a flat, flexible strip of plastic bags for receiving soiled surgical sponges. Each bag has a transparent front panel and a transparent or opaque rear panel joined by three connections, the first of which is located in the central, lower region of the bag, and is easily rupturable. The other two connections are located in the upper region of the bag intermediate the sides and the center and may be easily rupturable. The central connection, when intact, enables the bag to receive and segregate two sponges, and coacts with the other connections to limit gaping of the bag mouth. When the central connection is broken, the bag is enabled to receive a single, large sponge, and the two upper connections limit gaping.

5 Claims, 2 Drawing Figures

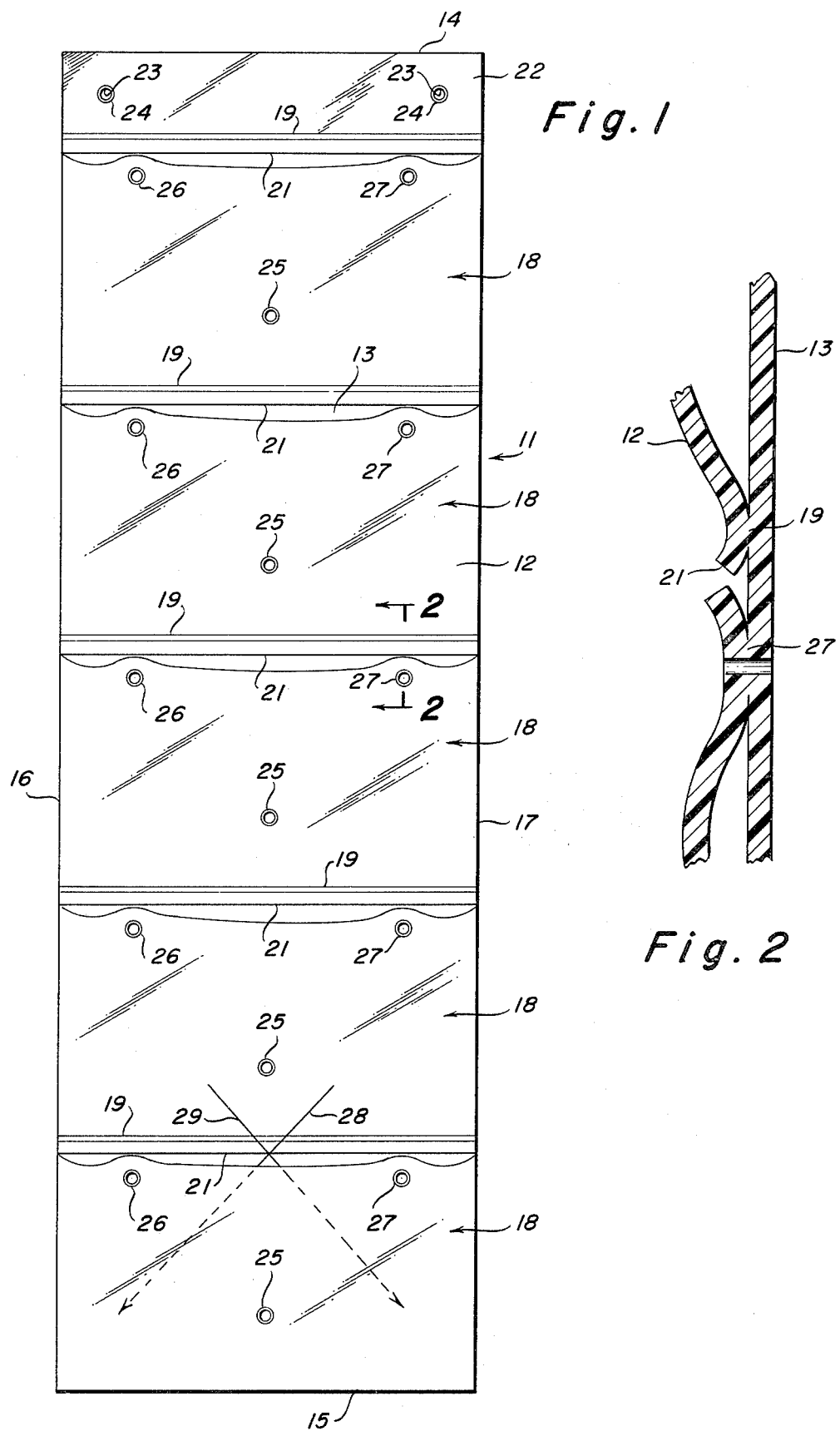

APPARATUS FOR HANDLING SOILED SURGICAL SPONGES

CROSS-REFERENCE TO RELATED APPLICATION

This application is a continuation-in-part of application, Ser. No. 31,839, filed Apr. 20, 1979, now abandoned.

BACKGROUND AND SUMMARY OF THE INVENTION

My U.S. Pat. No. 3,749,237, issued July 21, 1973, discloses an apparatus for handling soiled surgical sponges which comprise a flat, flexible strip of plastic bags. The front and rear panels of each bag are joined by an easily rupturable connection, which may be left intact to enable the bag to receive and segregate two small sponges, or broken to adapt the bag to receive a single, large sponge. The embodiment shown in the patent uses a connection in the form of a central longitudinal seam defined by an adhesive or a weak heat seal, whereas a commercial embodiment used simply a weak heat seal spot located in the central, upper region of the bag. Experience has shown that these forms of my sponge handling bag strip have one disadvantage, namely, the mouths of the bags tend to gape excessively, particularly when the bags are filled with large, blood-soaked sponges. This condition is considered undesirable because it permits too much contact between the soiled sponges and the atmosphere of the operating room.

The object of the present invention is to provide an improved form of the basic apparatus described in said patent in which the gaping condition just mentioned is materially reduced. According to the invention, the new bag strip employs three connections between the front and rear panels of each bag. The first connection of each set is located in the central, lower region of the bag and is easily rupturable. The other two connections may, but need not, be easily rupturable, and are located in an upper region of the bag intermediate the sides and the center. When the lower connection is intact, it enables the bag to hold in a segregated manner two small sponges, and coacts with the two upper connections to limit gaping of the bag mouth. On the other hand, when the lower connection is broken, the bag is enabled to receive a single, large sponge, and gaping of the mouth is limited solely by the two upper connections. Thus, the improved form of the bag strip provides the desirable characteristics of the prior forms while substantially eliminating their undesirable gaping characteristic.

During operations, the bag strips commonly are hung one behind another. Therefore, if both panels are transparent, sponges in an underlying bag can be seen through the foremost strip, and a busy sponge nurse may bypass an empty bag, thinking that it already has been used. As a result, an accurate final sponge count may be difficult to achieve. This situation can be eliminated, if necessary, merely by making the rear panel opaque.

BRIEF DESCRIPTION OF THE DRAWINGS

The preferred embodiment of the invention is described herein in detail with reference to the accompanying drawing, in which:

FIG. 1 is a plan view of the improved bag strip.
FIG. 2 is a sectional view, on an exaggerated scale, taken on line 2—2 of FIG. 1.

DESCRIPTION OF PREFERRED EMBODIMENT

The preferred bag strip 11 shown in the drawings is made from a flattened tube of clear polyethylene material approximately 2 mils thick, 10 inches wide, and 32 inches long. The strip comprises front and rear panels 12 and 13, respectively, which are joined by folds at the ends 14 and 15, and by heat seals which extend along the sides 16 and 17 and are formed as an incident to severing the strip from the tubular stock.

Strip 11 contains five sponge-receiving bags 18 which are defined by a series of uniformly spaced, transverse heat seals 19 interconnecting the front and rear panels 12 and 13. The bags measure approximately 6 inches by 10 inches, and have open mouths created by slits 21 in front panel 12 which extend between side margins 16 and 17 and each of which is located about ¼ inch below one of the seal lines 19. At its upper end, strip 11 has a two inch wide tab 22 containing a pair of holes 23. These holes enable the strip to be hung from pegs or hooks and are formed by heated probes which are punched through panels 12 and 13. This forming technique creates a narrow annular heat seal 24 between the panels which surrounds each hole and serves as a reinforcement.

Each of the bags 18 is provided with three additional connections 25-27 between the front and rear panels 12 and 13. The first connection 25 is located in the central, lower region of the bag, preferably at a point spaced from the bottom by a distance of about one-third the height of the bag, and it is made to be easily rupturable. It is preferred that this connection be a heat seal formed by the technique used to create mounting holes 23. The other two connections 26 and 27 are located in the upper region of the bag intermediate the sides 16 and 17 and the center. In particular, it is recommended that these connections be located about ½ inch below slit 21 at points spaced from the center of the bag by a distance of about three-tenths the width of the bag. Although it is not essential that connections 26 and 27 be easily rupturable, this is the preferred constuction because it is considered most convenient to form these connections in the same way as connection 25 and the mounting holes 23.

If lower connection 25 is intact, each bag may be used to hold two soiled sponges. The sponges are inserted through the central portion of the bag mouth bounded by connections 26 and 27 along the directions indicated by the arrows 28 and 29, and they are segregated sufficiently for the purpose of easy counting by connection 25. In this mode of use, the three connections 25-27 coact to limit gaping of the mouth. On the other hand, when large sponges are to be collected, lower connection 25 is broken manually, e.g., by inserting of the sponge nurse's fingers into the bag either before or as an incident to deposit of the soiled sponge. In this case, each bag 18 receives only a single sponge, and gaping of the mouth is limited solely by the upper connections 26 and 27.

It is evident that the connections 25-27 could be constructed in different ways. For example, adhesive spots or small Velcro type fasteners might be used in place of weak heat seals, and the localized upper connections 26 and 27 might be replaced by Ziplock type fasteners or heat seal bands which extend inward from the side margins 16 and 17 an inch or two along the mouth. However, none of these alternatives is recommended because they all appear more costly or otherwise less desirable than the simple, preferred construction.

As mentioned earlier, bag strips made entirely of clear (i.e., transparent) material may cause confusion which makes difficult an accurate sponge count. If this risk is considered serious, it can be eliminated by using an opaque rear panel 13 in the bag strip. In cases where the strip is formed from a flattened tube, the opaque agent can be introduced to the appropriate region during the tube blowing process. Alternatively, the strip can be made from separate, preformed opaque and clear plastic sheets which are heat sealed together.

I claim:

1. In an apparatus for handling soiled surgical sponges comprising a plurality of flexible plastic bags arranged in a flat strip and having front and rear panels, open mouths at their tops, and closed bottoms and sides, the improvement which comprises three connections between the front and rear panels of each bag, the first connection being located in the central, lower region of the bag and being easily rupturable, and the other two connections being located in the upper region of the bag at opposite sides of the center of the bag.

2. Apparatus as defined in claim 1 in which said first connection is spaced from the bottom of the bag a distance of about one-third the height of the bag, and each of the other two connections is spaced from the center of the bag a distance of about three-tenths the width of the bag.

3. Apparatus as defined in claim 1 in which all three connections are weak, easily rupturable heat seals.

4. Apparatus as defined in claim 2 in which all three connections are weak, easily rupturable heat seals.

5. Apparatus as defined in any one of claims 1-4 in which the front panel is transparent and the rear panel is opaque.